United States Patent [19]

Power

[11] Patent Number: 5,673,689
[45] Date of Patent: Oct. 7, 1997

[54] PISTON BASED VENTILATOR

[75] Inventor: John S. Power, Galway, Ireland

[73] Assignee: Puritan Bennett Corporation, Overland Park, Kans.

[21] Appl. No.: 705,083

[22] Filed: Aug. 27, 1996

Related U.S. Application Data

[63] Continuation of Ser. No. 386,159, Feb. 9, 1995, abandoned.

[51] Int. Cl.$^6$ .................................................. A61M 16/10
[52] U.S. Cl. ............................ 128/205.18; 128/204.18; 128/203.12
[58] Field of Search .................... 128/204.18, 205.18, 128/204.21, 203.12; 384/32; 417/259, 242

[56] References Cited

U.S. PATENT DOCUMENTS

| | | | |
|---|---|---|---|
| 1,406,141 | 2/1922 | Anston | 128/205.18 |
| 2,845,062 | 7/1958 | Kling et al. | |
| 3,669,097 | 6/1972 | Fitz | 482/1 |
| 3,727,524 | 4/1973 | Nishiyama et al. | 92/169.1 |
| 3,985,124 | 10/1976 | Coleman | 128/727 |
| 4,036,221 | 7/1977 | Hillsman et al. | 128/204.23 |
| 4,121,578 | 10/1978 | Torzala | 128/204.23 |
| 4,301,810 | 11/1981 | Belman | 128/720 |
| 4,448,192 | 5/1984 | Stawitcke et al. | 128/204.26 |
| 4,459,982 | 7/1984 | Fry | 128/204.23 |
| 4,462,410 | 7/1984 | Blais et al. | 128/727 |
| 4,487,207 | 12/1984 | Fitz | 482/1 |
| 4,587,967 | 5/1986 | Chu et al. | 128/204.21 |
| 4,617,637 | 10/1986 | Chu et al. | 364/505 |
| 4,726,366 | 2/1988 | Apple et al. | 128/204.21 |
| 4,823,788 | 4/1989 | Smith et al. | 128/205.24 |
| 4,957,107 | 9/1990 | Sipin | 128/204.21 |
| 4,971,049 | 11/1990 | Rotariu et al. | 128/204.21 |
| 5,104,694 | 4/1992 | DeVries | 427/255 |
| 5,107,830 | 4/1992 | Younes | 128/204.18 |

FOREIGN PATENT DOCUMENTS

| | | | |
|---|---|---|---|
| 41603 | 3/1910 | Australia | 128/205.18 |
| 1319175 | 6/1993 | Canada . | |
| 89731 | 12/1960 | Denmark | 128/205.18 |
| 818 186 | 9/1937 | France . | |
| 2 328 452 | 5/1977 | France . | |
| 28 22 030 | 12/1978 | Germany | 128/205.18 |
| 33 06 607 A1 | 9/1983 | Germany . | |
| 33 18 967 | 2/1984 | Germany | 384/32 |
| 1 541 852 | 3/1979 | United Kingdom . | |
| 2 054 387 | 2/1981 | United Kingdom . | |
| 2 121 292 | 12/1983 | United Kingdom . | |
| WO 92/14505 | 9/1992 | WIPO . | |

OTHER PUBLICATIONS

Younes, et al., "Proportional Assist Ventilation"; Am Rev Resp Dis 1992; 145: 121–129.

*Primary Examiner*—Vincent Millin
*Assistant Examiner*—Eric P. Raciti
*Attorney, Agent, or Firm*—Fulwider Patton Lee & Utecht, LLP

[57] ABSTRACT

A piston based ventilator for delivering breathing gas to the lungs of a patient, and more particularly a piston based ventilator that delivers breathing gas to a patient upon longitudinal movement of a piston rod and associated piston head within a piston cylinder. The piston rod is centrally located within the cylinder and moves along the cylinder in response to direct drive from a motor to move the piston head within the cylinder and displace a volume of gas to be delivered to the patient.

7 Claims, 3 Drawing Sheets

PISTON BASED VENTILATOR

This application is a continuation of application Ser. No. 08/386,159, filed Feb. 9, 1995, now abandoned.

BACKGROUND OF THE INVENTION

1. Field of the Invention

This invention relates generally to ventilators for delivering breathing gas to the lungs of a patient, and more particularly concerns a novel construction for a piston based ventilator used to deliver breathing gas to a patient.

2. Description of Related Art

Medical ventilators are widely utilized to provide breathing gas to a patient when the patient is unable to breath adequately without assistance. Such ventilators can be used for a wide variety of breathing strategies, including pressure assistance, which can be utilized when the patient has already begun an inspiratory effort, but is unable to fully complete the breath. One system in wide spread use for such ventilation is the piston type ventilator.

Early positive displacement ventilators utilized bellows systems to deliver a desired pressure and volume to a patient. These systems were quite effective, but had certain limitations which led to the design and construction of alternative mechanical constructions, including piston type ventilators.

Piston type ventilators known in the art commonly use a piston assembly wherein a piston head slides over a fixed central shaft. The gas to be delivered is drawn into cylinder through an inlet valve by the negative pressure created during the retraction of the piston and is subsequently delivered to the patient through an outlet valve by advancing the piston. In such a system, the volume of air delivered is directly related to the piston displacement within the cylinder. Conventionally, the piston head is connected to one or more piston rods which are driven by a motorized system to cause the piston head to move longitudinally over a fixed central shaft within the cylinder.

Piston lung ventilators known in the art also typically contain piston rings, usually a metal, plastic or composite ring for sealing the gap between the piston and the cylinder wall. In order to avoid excess friction, these piston rings frequently do not make a tight seal to the cylinder wall, allowing breathing gas with a high oxygen concentration to escape. For example, in a typical piston ventilator, the piston cylinder has a volume of about 2.7 liters, to allow for a loss of about 0.7 liters by leakage past the piston and compression of gas in the cylinder and in the delivery system, in order to still deliver up to 2.0 liters of breathing gas to the patient in one stroke of the piston. Due to the risk of fire, it is unsafe to allow oxygen enriched air to accumulate in the interior of an electrical product such as a ventilator. The breathing gas mixture to be delivered to the patient can also be diluted by the leakage, or 'blow by', of room air that leaks past the piston rings during the time the piston is retracting in order to draw breathing gas into the cylinder. Furthermore, the friction inherent in the use of piston rings requires more energy to operate the piston and increases stiction and friction of the piston-cylinder assembly.

Additionally, known piston ventilator designs usually contain one or more of the following elements: multiple linear bearings and seals located in the cylinder end plates that can, after wear, cause angular displacement and eventual tilt and interference between the piston and the cylinder; several stages of connection between the motor, piston rod and piston head which can cause backlash due to tolerance build up during operation of the system; bearing housings contained within the cylinder which decrease the volumetric capacity and piston displacement capability of the unit by reducing the stroke length of the piston head and attached rod. It can be understood that a piston for displacement of air that is self jigging to reduce tilt and interference, that would reduce the number of connections between the motor and the piston head and that would be a cost effective and easy to manufacture alternative to devices currently available would be novel in the art. The present invention meets these needs.

SUMMARY OF THE INVENTION

Briefly, and in general terms, the present invention provides for a novel piston based ventilator system for delivering breathing gas to a patient receiving assistance from the ventilator. The system of the present invention increases efficiency of the motor by decreasing the stages of connection and number of components required between the motor and the piston rod. Additionally, the number of seals needed to seal gaps between the piston rod and the cylinder is reduced.

In accordance with the invention, the present ventilator system supplies a flow of gas by movement of the piston head and a single connected piston rod along a center axis of the cylinder unit. Breathing gas from at least one intake valve enters into the cylinder when the piston head is displaced in a first longitudinal direction, creating negative pressure within the cylinder. Piston head movement in the opposite longitudinal direction causes piston head displacement of a volume of air to exit through a one-way outlet valve and to be supplied to a patient. The piston rod is fixed to the piston and orthogonal to the piston diameter, and extends longitudinally along the central axis of the cylinder, moving on two opposed bearings in opposing ends of the cylinder, with an optional seal located at the delivery end of the cylinder. The cylinder is not fitted with piston rings or seals and the piston fits within the cylinder with a close clearance gap (on the order of 50 microns) between the piston and the cylinder wall. The close clearance gap between the piston and the cylinder can be between 20 and 100 microns. By use of this design, the friction of cylinder to wall seals is eliminated and the number of seals for the piston rod is reduced to the minimum. To further eliminate friction and backlash in the system, a rack and pinion is used to drive the piston rod, with the rack cut onto the piston shaft and the pinion fixed to the end of the motor shaft.

The invention can advantageously include a self-jigging construction incorporating a precision linear bearing push fitted into a bearing cap in the end of the cylinder. The protruding portion of the bearing extends out of a flange and is fitted into a central hole in the cylinder end cap, which is then push fitted into the cylinder end. Since the end cap bearing surface is machined on the same setup as the inside diameter of the cylinder, the entire assembly is self aligning so that the bearing is concentric with the cylinder inside diameter. Concentricity of the piston can be further assured by grinding the piston outside diameter after assembly on the piston rod rack.

The benefits of the invention compared to prior art piston ventilators include resistance to jamming and distortion, ease of manufacture and assembly, more efficient use of the cylinder volume for breathing gas pumping, more compact design and elimination of a large portion of the friction, stiction and power loss of previous systems. The system is also more tolerant to wear, and will sustain efficient operation over a longer service life. These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
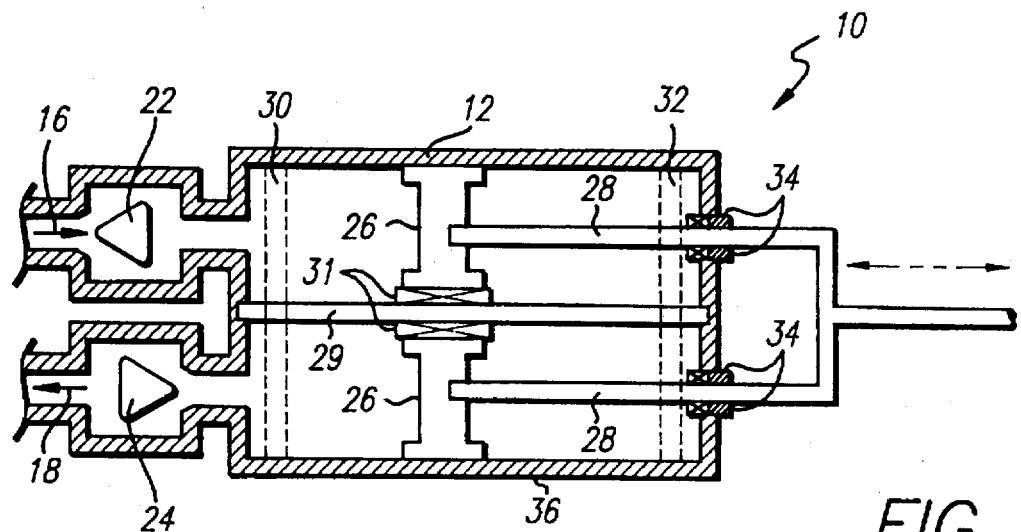
FIG. 1 is a diagram of a prior art single action piston ventilator.

As illustrated in the prior art drawing of FIG. 1, a typical prior art piston ventilator 10 includes a fixed volume cylinder 12 having a first gas delivery portion with an inlet 16 for receiving mixed breathing gas and an outlet 18 for delivering the mixed breathing gas to the patient during an inspiratory portion of a breath cycle. The inlet includes a check valve 22 allowing one way flow of mixed gas into the piston cylinder, and the outlet 18 similarly has a check valve 24 allowing one way flow of the mixed gas to the patient airway. A reciprocating piston head 26 is mounted to a piston rod 28 for moving the piston head and is movable within the cylinder between an extended position 30 in the first gas delivery position of the cylinder and a retracted position 32 in a second portion of the cylinder. The piston head glides along a center shaft 29 in the cylinder on bearings 31.

Figure 2:
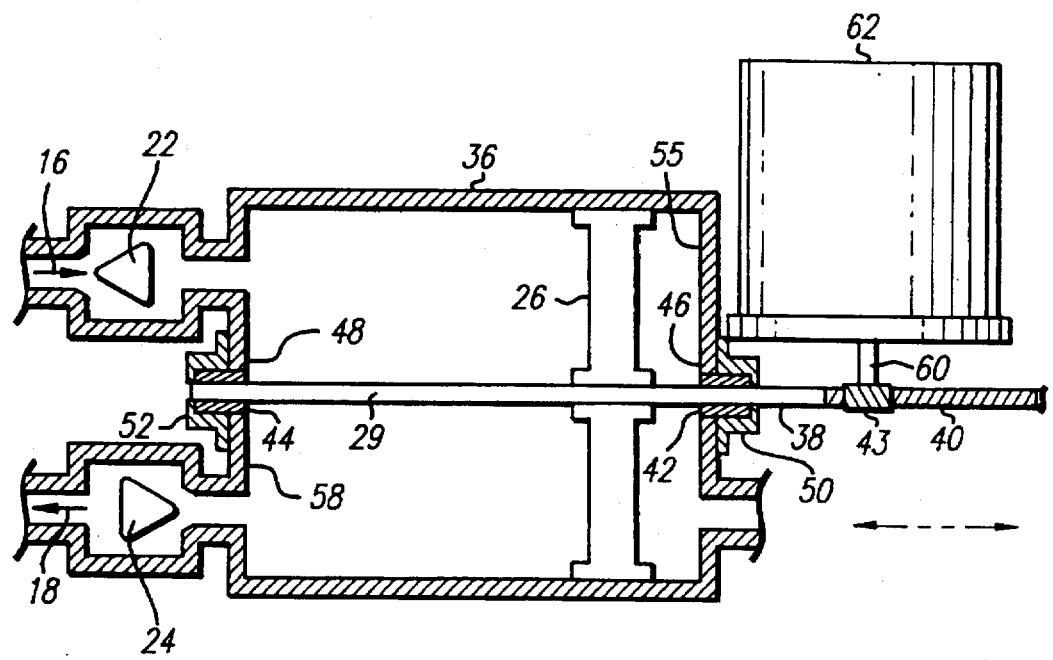
FIG. 2 is a diagram of a first embodiment of the piston ventilator of the invention.
Figure 3:
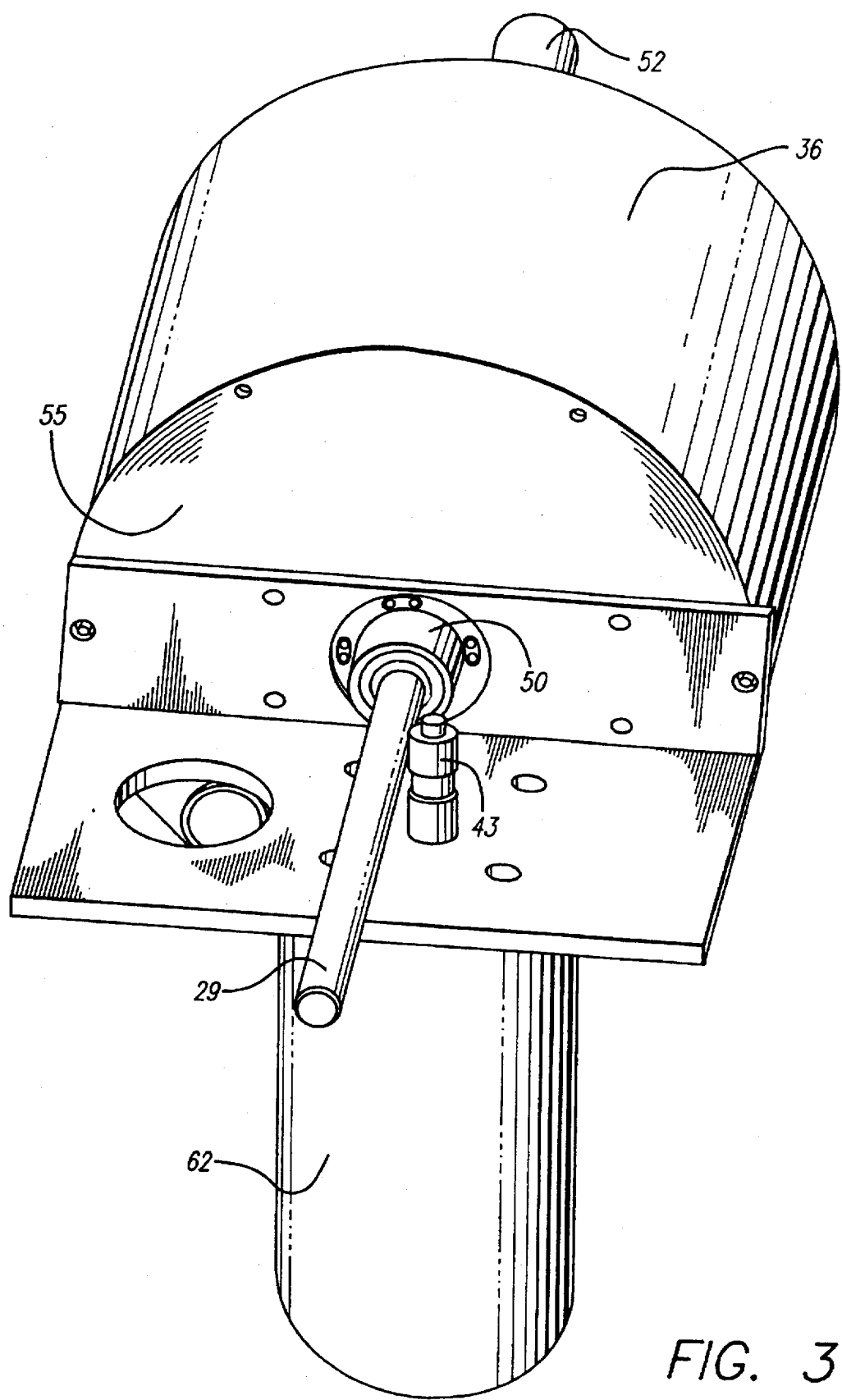
FIG. 3 is a perspective view of the piston based ventilator of FIG. 2.
Figure 4:
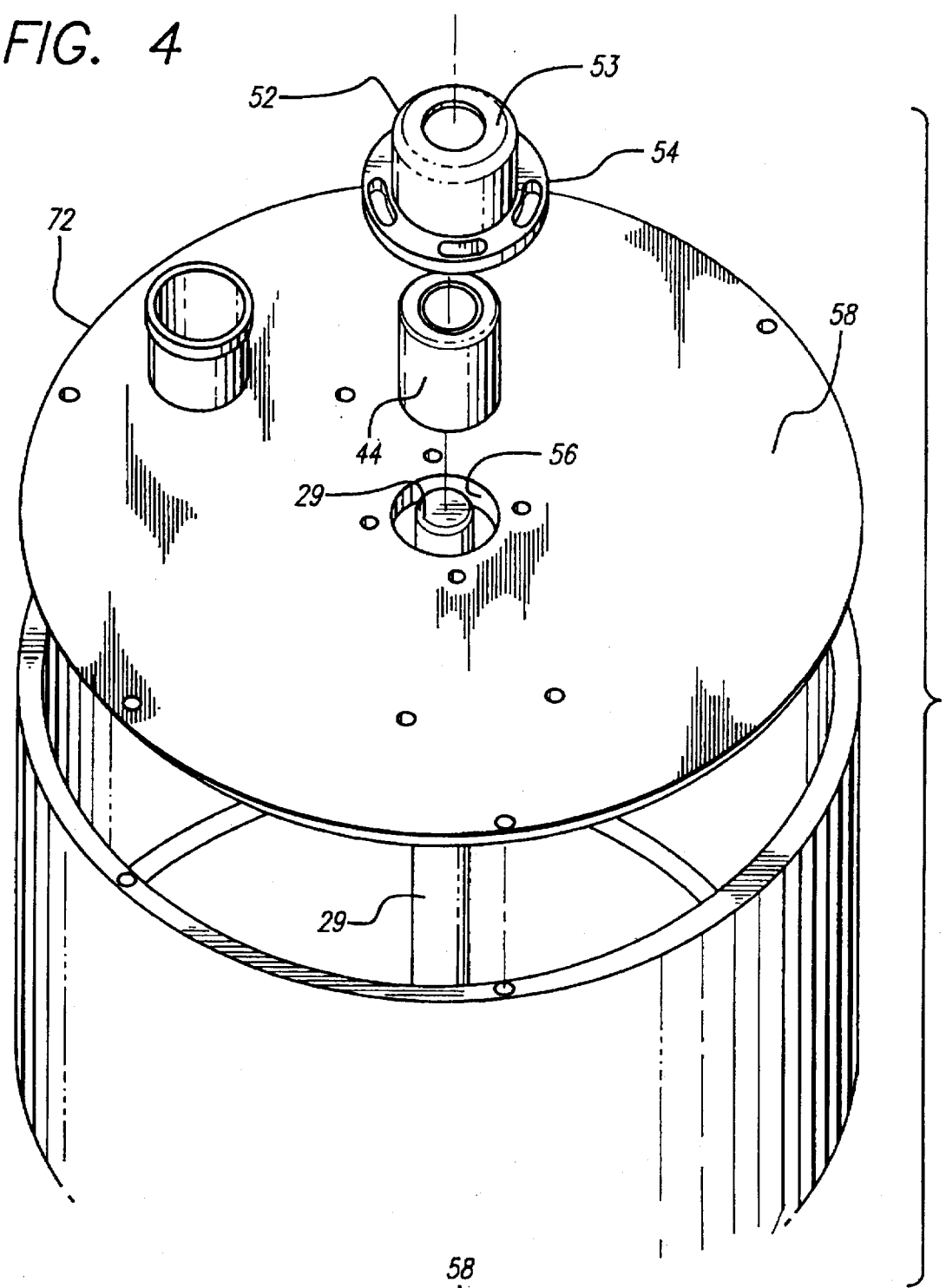
FIG. 4 is an exploded view of an end portion of the ventilator of FIG. 3.

A presently preferred embodiment of the present invention is illustrated in FIG. 2. The piston rod 29 is a single shaft concentric with the central axis of the cylinder 36. A portion of the piston rod 29 has an outer surface 38 containing tooth form cuts 40 to form a rack gear that engage a mating pinion gear 43 on rotating motor output shaft 60 that is rotated by motor 62. The output shaft 60 can be constructed to include a gear head or a gear reduction system to reduce the motor speed to a suitable speed for pinion gear 43 and thereby produce the desired piston speed. Upon rotation of the output shaft 60, the teeth on pinion gear 43 engage with the opposing teeth 40 on the piston rod 29 and cause the piston rod to move longitudinally in either direction as discussed above along the center axis of the cylinder. The piston head 26 is attached directly to the piston rod 29. By use of the invention, reciprocal longitudinal motion along only a single axis of the center cylindrical shaft 29 decreases the possibility of any tilting of the piston head 26 within the cylinder and possible axial misalignment. Valves 16 and 18 may contain, respectively, check valves 22 and 24 to regulate the flow of air to and from the cylinder during a breath cycle. Shaft 29 is slidably mounted along the cylinder center line and moves through precision linear bearings 42 and 44 located in opposite cylinder ends 46 and 48, respectively. Piston 26 is fixed to shaft 29.

The precision linear bearings 42 and 44 are push fitted into the close fit bearing caps 50 and 52, typically providing a narrow clearance distance between the center cylindrical shaft 29 and a return 53 on the rear of the bearing cap seal assembly, such as typically about 25 µm, for example.

Figure 5:
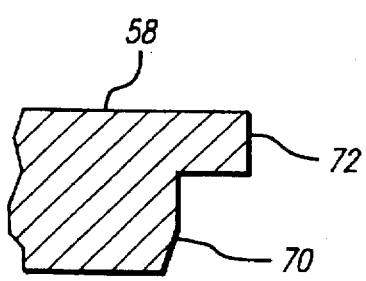
FIG. 5 is an enlarged view of a section of the edge of a self-jigging end cap of the ventilator of FIG. 4.

Alternatively, the piston shaft can be journalled in a close fit bearing cap providing a narrow clearance distance, thus eliminating the need for a seal altogether, and providing for a small but acceptable leak through the clearance, but removing significant sources of friction. The assembly is such that the bearing 44 protrudes out from the end of the bearing cap 52. Bearing cap 52 includes a flange 54 for mounting to the cylinder end cap 58, such as by bolts. The bearing cap 50 is typically mounted to the cylinder end cap 55 in the same fashion. This protruding portion of the bearing 44 is in turn push fitted into a central hole 56 in the cylinder end cap 58. Finally, the self-jigging cylinder end cap 58 is push fitted into the cylinder 36. The importance of this is that the end cap bearing hole 56 is bored at the same machine setting as the chamfered location step 70 on its periphery 72 illustrated in FIG. 5, and is therefore truly concentric. When assembled this further ensures that the bearing is located concentrically about the inner diameter of the cylinder and that the rack/piston assembly is located again concentric to the cylinder inner diameter. The peripheral edge of the piston is ground after being assembled to the rack, again ensuring concentricity.

A number of benefits accrue from the present invention. Unlike the prior art, the system is self-jigging during assembly and the piston can maintain close wall tolerances with the cylinder without concern for cocking or misalignment. Also, the volume of the cylinder is more efficiently used for a given stroke, since less of the volume is taken up with piston rod apparatus. Another advantage is that the system utilizes less seals and bearings, thus resulting in finer sources for friction and stiction. Since there are fewer parts and fewer machine operations, the invention is also more economical to manufacture and assemble.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A piston based ventilator system for providing breathing gas to a patient airway comprising:

a source of said gas for providing a supply flow of said breathing gas;

a fixed volume cylinder including first and second cylinder ends and a movable center shaft slidably mounted therein, said first and second cylinder ends comprising first and second self-jigging end caps each defining axially located concentric bearing holes providing a narrow clearance gap between said bearing holes and said movable center shaft, and first and second bearing caps mounted to said first and second end caps, respectively, each of said bearing caps having a close fit opening therethrough for slidably receiving said shaft, and providing means for minimizing leakage of said breathing gas through a gap defined between said shaft and said bearing caps, said cylinder having inlet valve means to allow flow of said gas into said cylinder and outlet valve means allowing flow of said gas to the patient airway;

a piston head fixed to said shaft such that motion of said shaft along said cylinder centerline provides means for moving said piston head longitudinally between said first and said second ends of said cylinder, wherein said movement of said piston head from said first end to said second end displaces a volume of said gas to be delivered to the patient airway and said movement from said second end to said first end causes said gas to be drawn into said cylinder.

2. The piston based ventilator system of claim 1, wherein said means for moving said piston rod comprises:

a rotary motor head; and first inter-engagement means located on a surface of said piston rod for engaging said piston rod with said rotary motor head, and second inter-engaging means located on a surface of said rotary motor head opposing said first inter-engagement means for engaging said rotary motor head with said piston rod, whereby when said rotary head rotates in a first direction it engages with said inter-engagement means on the surface of the piston rod to move said piston rod in a longitudinal direction and when said rotary head rotates in a second direction, said piston rod moves in an opposite longitudinal direction.

3. The piston based ventilator system of claim 1, wherein said inlet valve means comprises a check valve.

4. The piston based ventilator system of claim 1, wherein said outlet valve means comprises a check valve.

5. The piston based ventilator system of claim 1, wherein a clearance distance between 20 and 100 microns exists between the interior wall of said cylinder and the exterior diameter of said piston.

6. The piston based ventilator system of claim 5 wherein said clearance distance is approximately 50 microns.

7. The piston head based ventilator system of claim 1, wherein said bearing cap assembly includes a linear bearing.

* * * * *